(12) United States Patent
Simpson et al.

(10) Patent No.: US 6,415,044 B1
(45) Date of Patent: Jul. 2, 2002

(54) NON-DESTRUCTIVE INSPECTION METHOD FOR AN IMPACT TREATED SURFACE

(75) Inventors: Roger S. Simpson, Northville; Donald K. Cohen, Farmington Hills, both of MI (US)

(73) Assignee: Advanced Material Processing, Wayne, MI (US)

( * ) Notice: Subject to any disclaimer, the term of this patent is extended or adjusted under 35 U.S.C. 154(b) by 0 days.

(21) Appl. No.: 09/222,134

(22) Filed: Dec. 29, 1998

(51) Int. Cl.[7] .................................................. G06K 9/00
(52) U.S. Cl. ...................................................... 382/108
(58) Field of Search ................................. 382/100, 108, 382/141, 152; 356/237.1, 237.2, 237.5, 237.6, 234.3; 348/86, 92; 422/119, 120, 122, 292; 700/108, 109, 110; 73/104, 105; 250/306, 307, 336.1, 338.1, 340, 341.1, 341.8, 347, 424, 492.1, 492.3

(56) References Cited

U.S. PATENT DOCUMENTS

| | | | |
|---|---|---|---|
| 2,958,925 A | 11/1960 | Roberts | 29/90.7 |
| 3,950,642 A | 4/1976 | Feld | 250/302 |
| 4,287,416 A | 9/1981 | Kramer et al. | 378/72 |
| 4,402,227 A | 9/1983 | Hayashi et al. | 73/812 |
| 4,432,220 A * | 2/1984 | Loersch et al. | 72/53 |
| 4,709,383 A | 11/1987 | Goto et al. | 378/72 |
| 5,003,805 A | 4/1991 | Thompson | 72/53 |
| 5,127,019 A * | 6/1992 | Epstein et al. | 372/108 |
| 5,172,580 A | 12/1992 | Thompson | 72/53 |
| 5,176,018 A | 1/1993 | Thompson | 72/53 |
| 5,235,517 A | 8/1993 | Thompson et al. | 700/204 |
| 5,272,746 A | 12/1993 | Isobe et al. | 378/72 |
| 5,293,320 A | 3/1994 | Thompson et al. | 700/160 |
| 5,490,195 A | 2/1996 | Berkley | 378/72 |
| 5,581,483 A | 12/1996 | Thompson et al. | 702/719 |
| 5,596,912 A * | 1/1997 | Laurence et al. | 76/107 |
| 5,625,664 A | 4/1997 | Berkley | 378/72 |
| 5,790,620 A * | 8/1998 | Okazaki et al. | 376/305 |
| 6,030,829 A * | 2/2000 | Dannoux et al. | 435/288.3 |
| 6,094,260 A * | 7/2000 | Rockstroh et al. | 356/35.5 |

FOREIGN PATENT DOCUMENTS

EP 0497610 A2 1/1992 .......... G01B/21/30

* cited by examiner

Primary Examiner—Andrew W. Johns
Assistant Examiner—Shervin Nakhjavan
(74) Attorney, Agent, or Firm—Harness, Dickey & Pierce, P.L.C.

(57) ABSTRACT

A nondestructive method and apparatus for the inspection of impact treated surfaces to predict impact treatment process variables which acquires a multi-dimensional map of an impact treated surface, characterizes the multi-dimensional map to develop surface texture parameters, and develops relationships between the surface texture parameters and the impact treatment process variables.

25 Claims, 4 Drawing Sheets

NON-DESTRUCTIVE INSPECTION METHOD FOR AN IMPACT TREATED SURFACE

BACKGROUND OF THE INVENTION

The present invention relates to a method for nondestructively determining the performance characteristics of a metal component. More specifically, the present invention relates to linking impact treatment process variables to surface texture and determining the impact process' reliability and reproducibility of process variables linked to fatigue life, stress corrosion resistance enhancement, or other related performance parameters of an impact treated or shot peened metal component.

Impact treatment processes, including shot peening, have long been known to be capable of developing large fatigue strength and/or stress corrosion resistance enhancements in cyclically stressed metallic workpieces. In addition, such processes are known to be capable of generating certain workpiece surface morphology characteristics which are advantageous in certain applications.

Impact treatment processes used to improve workpiece performance include shot peening, sand blasting, laser shock processing and any other such processes which produce surface plastic deformation resulting from the surface being impacted with relatively high energy. Such impact treatment processes enhance the performance characteristics of a component through modification of a component's surface and subsurface characteristics. During the shot peening process, a stream of shot or other near spherical particles typically made of a metal or glass travelling at high velocity is directed at a component surface. The shot is directed at the component so as to cause plastic deformation and strain of the component surface. Similarly, lasers which generate high energy are used to impact treat surfaces by generating plastic deformation and strain. Plastic strain is the mechanism where the surface of the component is put into a state of compressive residual stress, increased dislocation density, and other metallurgical microstructural changes, these being key to the life enhancing benefits of impact treatment processes. Depending on the nominal, range, and distribution of the values of certain critical impact treatment process variables or parameters such as in shot peening where shot size, shot velocity, shot impact angle, and workpiece shot peen process saturation are critical variables, the shot peen process induces different magnitudes and depths of residual compressive stresses and microstructural changes and varying degrees and types of surface morphology characteristic changes. In laser shock processing, variables such as laser intensity and the number of impacts or "shots" in a given area determine the level of the desired workpiece characteristics. Each of these impact process induced surface and subsurface changes and enhancements are quantitatively and reliably related to impact process variable's nominal, range, and distribution values for given workpieces of given chemical and physical characteristics. These relationships are well established in the art, particularly in shot peening.

Due to the shot peening processes total number of critical process parameters and the total number of ways changes in those variable values can be affected during processing, the shot peen process has developed a history of variability in process induced benefit when applied to workpieces in a production processing environment. This is true unless a very high degree of care is taken to positively and systematically control all shot peen process variables within relatively narrow tolerances.

The current best available method of defining what shot peen process should be applied to test workpieces and/or predicting whether a workpiece processed in a production application of shot peening would perform as well as expected is to determine the magnitude of the residual stresses introduced by the shot peen process, in profile and in depth, through x-ray diffractometer analysis, a technique well documented in the art. This is, however, a destructive inspection process as it requires extensive electrochemical milling of the surface being analyzed. It is also relatively costly and time consuming enough to be ineffective as a real time production inspection technique.

The standard industry accepted method of inspecting and calibrating a shot peen process involves the exposure of an SAE 1070 steel strip (Almen strip) to the blast stream of shot. This strip is mounted by four retaining screws on a thick block and placed in the blast in a manner which best represents the workpiece surface for the same exposure time the workpiece will experience. As an Almen strip is exposed to the blast stream, it arcs towards the stream. The amount of arc when stabilized over time (Almen saturation) indicates the total energy of the blast stream. The shot peen process cycle time is also typically determined by and/or calculated from the exposure time required to achieve Almen saturation utilizing Almen strips. This is a technique well established in the prior art.

While Almen intensity is an indicator of total blast stream energy, the method has significant shortcomings as a valid non-destructive inspection of the efficacy of a shot peen process in developing workpiece fatigue strength and/or other shot peen processes induced workpiece performance enhancements. First, the Almen strip is rarely of the same material or hardness as the workpiece. Second, it is only representative of the shape of a workpiece if that workpiece's area being shot peened is essentially flat. As such, an Almen strip, which is intended to be only a representation of the workpiece being processed, is also typically a very poor representation of the workpiece. Additionally, the total cumulative inherent measurement system variability of the Almen measurement system as specified in industry and U.S. military specifications has been documented in the prior art as being large enough to often exceed the total allowable manufacturing process tolerances for the shot peen process it is attempting to calibrate and measure.

While there are several other serious drawbacks and shortcomings to the Almen system of shot peen process measurement, which are well documented in the art, perhaps most importantly the height of an Almen strip at Almen saturation (Almen intensity) measures only the aggregate energy transfer to the Almen strip by the shot peen process in the form of residual compression. This aggregate residual compression is the aggregate effect of the nominal, range, and distribution values of all of a shot peen processes variables experienced during the processing of the Almen strip. An Almen intensity value as such cannot indicate what the nominal residual compression is at any given point on the surface and/or subsurface respectively. This effectively precludes the Almen system from measuring the individual level and effect of any or all shot peen process parameters. Thus, process parameters such as shot size, shot velocity, and shot angle of impact, cannot be predicted individually or quantitatively predicted by the Almen technique without unequivocally knowing the quantitative value of the other process parameters and the quantitative level of variability and measurement caused by cumulative measurement of variability. For example, one may deliver the same aggregate amount of energy to the workpiece by using large shot at a small velocity or small shot at a high velocity. In either case, the Almen strip can indicate the same effective measurement. As such, a given Almen intensity value can be arrived at through an infinite combination of process parameter nominal and range values, each combination having it's own unique pattern of residual stress magnitude in depth and in profile. Since the magnitude and depth of residual compression and other shot peen process induced workpiece changes are highly related to workpiece fatigue strength and other shot peen process induced workpiece benefits, the Almen measurement system cannot be counted on to quantitatively correlate a shot peen process with the desired level of benefits it is intended to induce in the workpieces. This phenomena is well established in the prior art.

For a given workpiece of given chemical and physical characteristics, a given shot particle of given size impacts a metallic workpiece surface at a specific impact angle and velocity, leaving a unique indentation mark or "fingerprint". As multiple shot particles impact the same general area, the workpiece surface in that area becomes increasingly covered with indentations. As subsequent shot impact indentations overlap previous indentations, some of the workpiece surface morphology characteristics of shot impact associated with shot of given shot peen process variable levels change. However these changes are reliably predictable for given workpiece saturation levels.

With statistically capable controls on key variables such as shot size and velocity, the variability from a peening operation in terms of results such as fatigue strength enhancement and surface texture development may be reduced. However, without destructively testing the workpiece, when inspecting a shotpeened workpiece, one is never totally assured of the stability of shot peen process induced fatigue strength and/or stress corrosion resistance improvements offered by the peening process the workpiece experienced. It is never totally assured that critical process parameter levels did not vary unacceptably during processing. The ability to assure that a surface has been properly treated by a shot-peening process relies on statistical controls of all peening variables. However, there is no absolute certainty that the "effective" parameter (e.g. shot velocity) as measured by a sensor and controller is that which the workpiece actually experienced. Accordingly, a technique is needed to assess impact treated or shot peened workpieces to assure that the desired peening conditions have all been met and thus the fatigue and corrosion resistance advantages expected are present in the workpiece being assessed.

SUMMARY OF THE INVENTION

The present invention is the first effective nondestructive inspection (NDI) technique for the analysis of an impact treated or shot peened surface. The basis of this NDI technique is the assumption that after being impacted, a surface contains the "fingerprint" of the impact process and/or individual impacts in the generated surface texture. For example, a surface shot peened with smaller diameter shot will tend to have smaller diameter craters as compared to a surface peened with larger shot. Thus, the NDI technique requires the ability to discern quantitatively, those aspects of the surface texture that may be best related to the impact parameters.

While shot peening is the primary method of surface treatment analyzed in the present invention to improve the performance of metal workpieces, alternate surface treatment methods, such as laser or other electromagnetic surface treatments, exist to which the present invention may be applied. In laser surface treatment, a laser is directed at the surface of a workpiece typically covered with a black paint, causing a high energy shock wave to be directed into the workpiece generating plastic deformation and residual compressive stresses in the surface and subsurface of the workpiece, similar qualitatively to the effect of shot peening.

With the advent of the powerful desk top computer and various advanced analytical software packages, it is now possible to apply an intense amount of analysis to the impact treatment process. The present invention provides an NDI technique that is capable of predicting the impact treatment process variables experienced on an impact processed surface or workpiece. From such information, provided that performance enhancement characteristics are known for a given impact process of a given parameter values and tolerances for the workpiece in question, the presence or absence of such performance characteristics as increased fatigue life and stress corrosion resistance enhancement can be identified at the workpiece level. The present invention comprises a method and apparatus to analyze the surface texture characteristics of an impact treated component to determine and predict the quantitative level of impact treatment process parameters experienced on the analyzed surface or workpiece during its impact processing.

Through development of a data base that quantitatively relates shot peen process variable levels to certain workpiece chemical and physical characteristics, and the resultant residual stresses in profile, surface morphology characteristics of a shot peened workpiece of known chemical and physical characteristics can reliably predict the magnitude of residual stresses in profile and in depth induced by the shot peen process the workpiece experienced. For example, after the process parameter values are determined on an impact treated workpiece, empirical data in the database linking the process variables to performance critical characteristics such as residual stress can be used based on established test data to predict the actual performance characteristics of the analyzed workpiece.

This new NDI technique takes advantage of developments in high speed two dimensional (2D) and three dimensional (3D) non-contact surface profilometry to provide detailed images of the impact treated or peened surfaces. The NDI approach incorporates statistical analysis such as designed experiments (DOE), correlation analysis, principal component analysis, and multiple regression (MREG), all available in common commercial software. The present invention is the first effective NDI technique for the analysis of an impact treated or shot peened surface.

In summary, a first embodiment of the invention may be described as a nondestructive method for the inspection of impact treated surfaces to predict impact treatment process parameter levels and tolerances experienced during impact treatment processing on the workpiece being inspected comprising: acquiring a multi-dimensional map of an impact treated surface, characterizing the multi-dimensional map to develop surface texture parameters, and developing relationships between the surface texture parameters and the quantitative impact treatment process parameter levels experienced. In a second embodiment, the invention may be described as an apparatus for determining the impact treatment process parameter levels of an impact treated surface comprising: an imaging system which captures the surface texture of the impact treated surface in a multi-dimensional image, a processor which analyzes the multi-dimensional image to isolate a plurality of statistically independent variables, where the statistically independent variables describe the surface texture of the impact treated surface and are used to predict the impact treatment process parameter levels and tolerances.

Further objects, features, and advantages of the invention will become apparent from a consideration of the following description and the appended claims when taken in connection with the accompanying drawings.

DETAILED DESCRIPTION OF THE PREFERRED EMBODIMENT

The following description of the present invention is merely exemplary in nature and is in no way intended to limit the invention or its uses. Moreover, the following description, while depicting the analysis of a shot peened surface, is intended to adequately teach one skilled in the art to analyze any impact treated surfaces or surface treatment.

The first step in the method of the present invention is to create a designed experiment (DOE) which systematically varies the impact treatment or shot peening parameters experience by a surface or workpiece. There are a number of peening parameters which may be varied but in the preferred mode the shot velocity, shot angle of impact, saturation level, and shot size are varied. A sample DOE is run showing the following tables. A sample DOE run is shown by the following table. The DOE is usually run a plurality of times.

TABLE 1

RUN CONDITIONS

| RUN # | Shot Velocity (PSI) | Shot Angle of Impact (degrees to normal) | Saturation Level (%) | Shot Size CW (mils) |
|---|---|---|---|---|
| 1 | 40 | 45 | 100 | 12 |
| 2 | 75 | 45 | 100 | 12 |
| 3 | 40 | 90 | 100 | 12 |
| 4 | 75 | 90 | 100 | 12 |
| 5 | 40 | 45 | 200 | 12 |
| 6 | 75 | 45 | 200 | 12 |
| 7 | 40 | 90 | 200 | 12 |
| 8 | 75 | 90 | 200 | 12 |
| 9 | 40 | 45 | 100 | 28 |
| 10 | 75 | 45 | 100 | 28 |
| 11 | 40 | 90 | 100 | 28 |
| 12 | 75 | 90 | 100 | 28 |
| 13 | 40 | 45 | 200 | 28 |
| 14 | 75 | 45 | 200 | 28 |
| 15 | 40 | 90 | 200 | 28 |
| 16 | 75 | 90 | 200 | 28 |

Figure 1A:
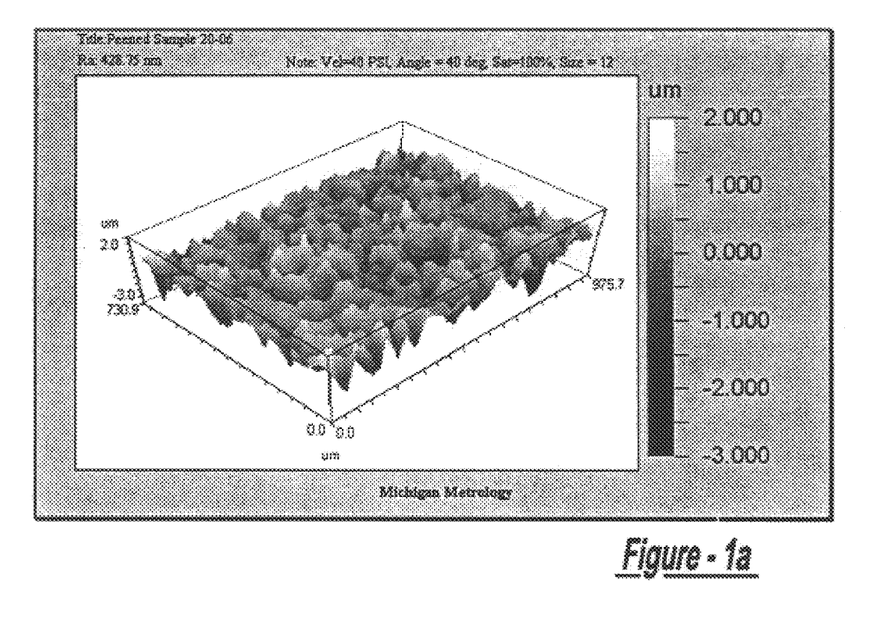
FIGS. 1a and 1b are sample three dimensional profiles of a shot-peened surface.
Figure 1B:
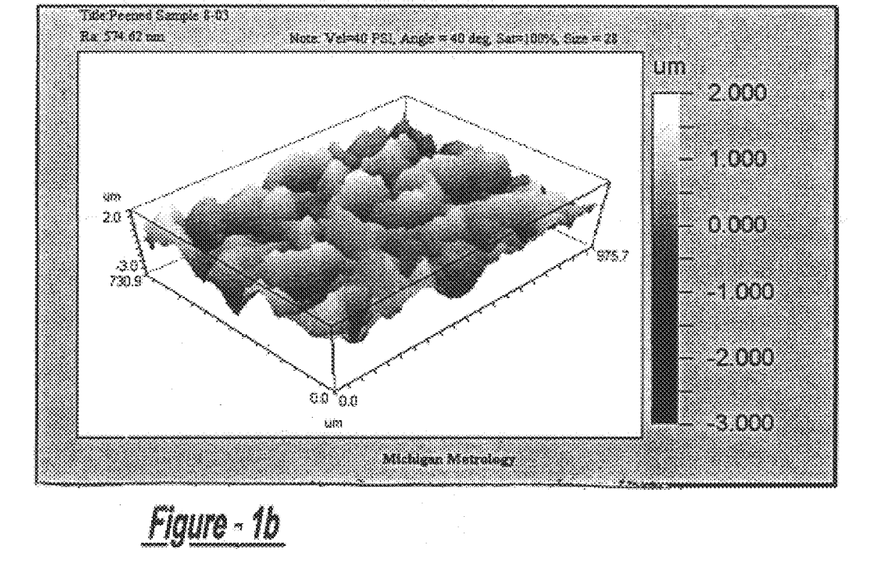

Once the surfaces have been peened, 2D or 3D surface maps over the peened areas are acquired, as seen in FIGS. 1a and 1b. These maps include lateral information (i.e. "x and y" coordinates) and height (i.e. "z" coordinate) information of the surface. Typically 10 different 1 mm ×1 mm regions of the peened sample are acquired and stored for post processing and archival. The present surface data was compiled utilizing the WYKO RST system. However, any other instruments may be used which are able to resolve the surface features. FIGS. 1a and 1b demonstrate the measurement of two surfaces peened with different size shot at nominally the same angle of impact, shot velocity and saturation levels. While camera systems capturing 3D images of the surface are preferred, 2D information may also be used by the present information. Such information in one embodiment of the present invention may be generated by a mechanical means.

Mechanical means for measuring surface treatment exist in the form of profilometers which use a mechanical sensor or stylus for non-destructively measuring the surface texture, including obtaining profile data of a shot-peened workpiece surface and determining total plastic upset depth for a selected dent. A topogram of a shot peened surface is obtained in the form of an x-y plot (only two dimensions) generated by the profilometer scanning a line across a treated surface. From the profilometer measurement, a peak to valley depth of a selected indentation is obtained. Using this data a 2D image or map of the subject surface may be acquired.

Once the surface maps are acquired, a series of algorithms are applied to the data to characterize the surface texture. Numerous variables are used to characterize the surface texture and are included in the following Table 2. Further variables are defined in the ANSI/ASME B46.1-1995 standard and are considered within the scope of this invention.

TABLE 2

| Term | Definition |
|---|---|
| Rsk | Symmetry of surface materials above or below the mean level |
| Rku | Kurtosis, or the distribution of peaks and valleys. |
| Rt | The difference in height between the highest peak and lowest valley on the surface. |
| Stylus Y λq | Measure of spatial wavelengths that comprise the surface. |

Once these various surface texture parameters are evaluated, the next task is to find four (or more) independent texture parameters. If the parameters are statistically independent, then it is possible that in some combination they each describe a unique feature of the peening process (e.g. shot size). Using four texture parameters the present invention can ultimately predict certain process parameters such as shot size, shot velocity, saturation, and shot angle, but is not limited to just these process parameters. The independence of the parameters is found by evaluating the degree of correlation. For example $r^2>0.8$ is usually considered good correlation. Thus for this work we seek $r^2$ values as close to zero(0) between the various parameters.

A correlation matrix is formed of all parameters against each other. For this work, the correlation matrix, as shown in Table 3, is scanned for four or more parameters that demonstrate minimum correlation between each other. A subset of the correlation matrix is also presented in the following table, with the four parameters chosen for this work highlighted.

Table 3 is a depiction of the correlation matrix(a) for various surface texture parameters. The correlation results for the four parameters (b) selected by a correlation program routine is depicted. The parameters and their correlation values based on earlier work (C) is presented and are used in this illustration of the procedure.

TABLE 3

Correlation Analysis

| | Ra | Rq | Rsk | Rku | Rpm | Rvm | Rz | Rp | Rv | Rt | Mr1 | Stylus X S | |
|---|---|---|---|---|---|---|---|---|---|---|---|---|---|
| Ra | 1.00 | 1.00 | 0.40 | 0.43 | 0.84 | 0.88 | 0.88 | 0.62 | 0.74 | 0.70 | 0.41 | 0.62 | A |
| Rq | 1.00 | 1.00 | 0.38 | 0.39 | 0.86 | 0.90 | 0.90 | 0.65 | 0.77 | 0.73 | 0.41 | 0.59 | |
| Rsk | 0.40 | 0.38 | 1.00 | 0.66 | 0.29 | 0.05 | 0.16 | 0.11 | 0.10 | 0.00 | 0.45 | 0.43 | |
| Rku | 0.43 | 0.39 | 0.66 | 1.00 | 0.02 | 0.03 | 0.02 | 0.31 | 0.25 | 0.29 | 0.11 | 0.69 | |
| Rpm | 0.84 | 0.86 | 0.29 | 0.02 | 1.00 | 0.92 | 0.97 | 0.94 | 0.89 | 0.94 | 0.22 | 0.24 | |
| Rvm | 0.88 | 0.90 | 0.05 | 0.03 | 0.92 | 1.00 | 0.98 | 0.83 | 0.96 | 0.93 | 0.50 | 0.32 | |
| Rz | 0.88 | 0.90 | 0.16 | 0.02 | 0.97 | 0.98 | 1.00 | 0.90 | 0.95 | 0.95 | 0.39 | 0.29 | |
| Rp | 0.62 | 0.65 | 0.11 | 0.31 | 0.94 | 0.83 | 0.90 | 1.00 | 0.89 | 0.97 | 0.13 | 0.03 | |
| Rv | 0.74 | 0.77 | 0.10 | 0.25 | 0.89 | 0.96 | 0.95 | 0.89 | 1.00 | 0.97 | 0.48 | 0.11 | |
| Rt | 0.70 | 0.73 | 0.00 | 0.29 | 0.94 | 0.93 | 0.95 | 0.97 | 0.97 | 1.00 | 0.32 | 0.04 | |
| Mr1 | 0.41 | 0.41 | 0.45 | 0.11 | 0.22 | 0.50 | 0.39 | 0.13 | 0.48 | 0.32 | 1.00 | 0.50 | |
| Stylus X S | 0.62 | 0.59 | 0.43 | 0.69 | 0.24 | 0.32 | 0.29 | 0.03 | 0.11 | 0.04 | 0.50 | 1.00 | |

Final Four Selection of "Independent" parameters
Correlation Analysis

| | Rsk | Rt | Mr1 | Stylus X S | |
|---|---|---|---|---|---|
| Rsk | .48 | 0.48 | 0.45 | 0.43 | B |
| Rt | 0.48 | 1 | 0.32 | 0.04 | |
| Mr1 | 0.45 | 0.32 | 1 | 0.20 | |
| Stylus X S | 0.43 | 0.04 | 0.20 | 1 | |

Final Four Selection of "Independent" parameters
Correlation Analysis

| | Rsk | Rku | Rt | Stylus Y $\lambda$q | |
|---|---|---|---|---|---|
| Rsk | 1 | 0.61 | 0.48 | 0.22 | C |
| Rku | 0.61 | 1 | 0.74 | 0.22 | |
| Rt | 0.48 | 0.74 | 1 | 0.33 | |
| Stylus Y $\lambda$q | 0.22 | 0.22 | 0.33 | 1 | |

Figure 2:
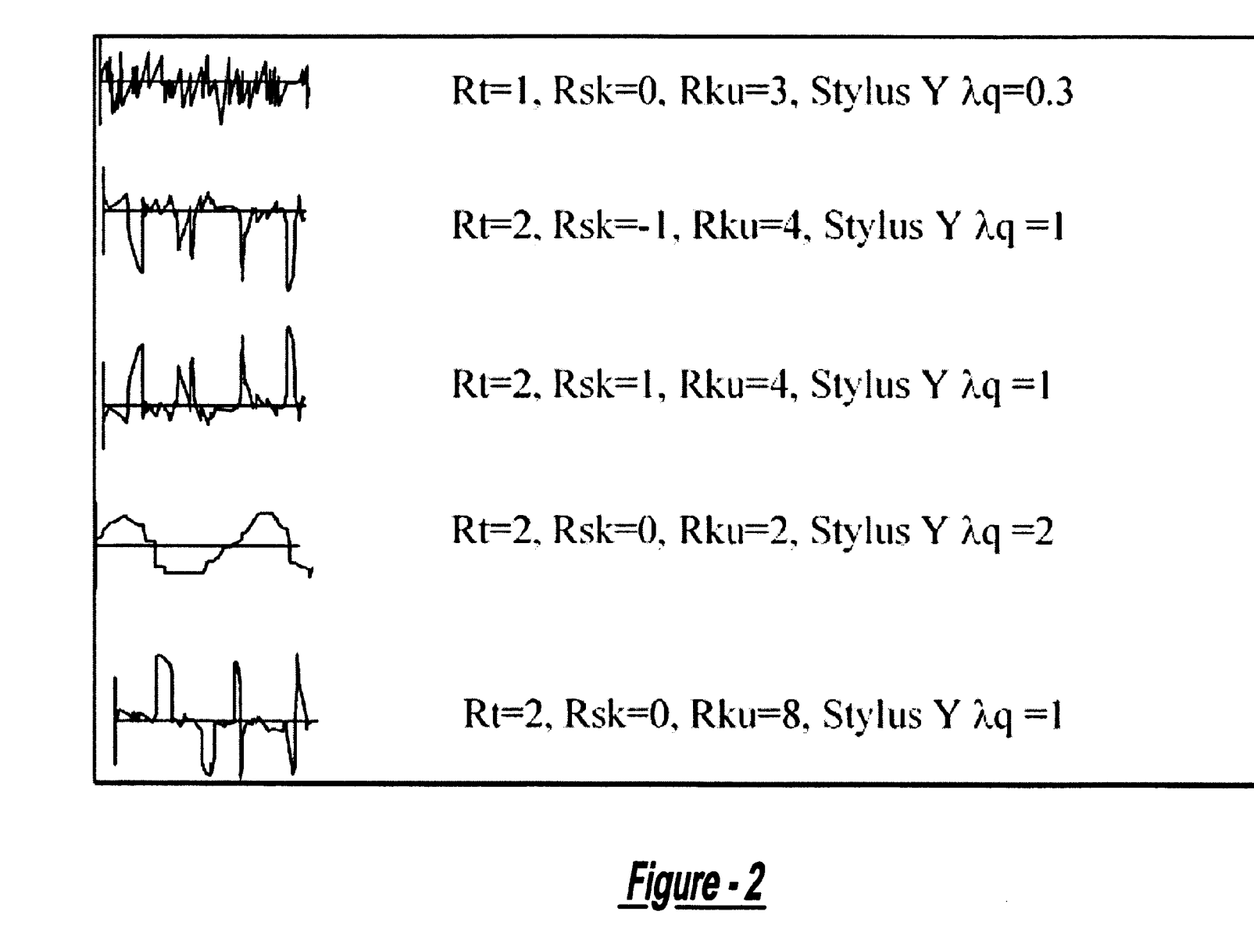
FIG. 2 is a pictorial example of the relationship between surface variables and surface texture.
Figure 3A:
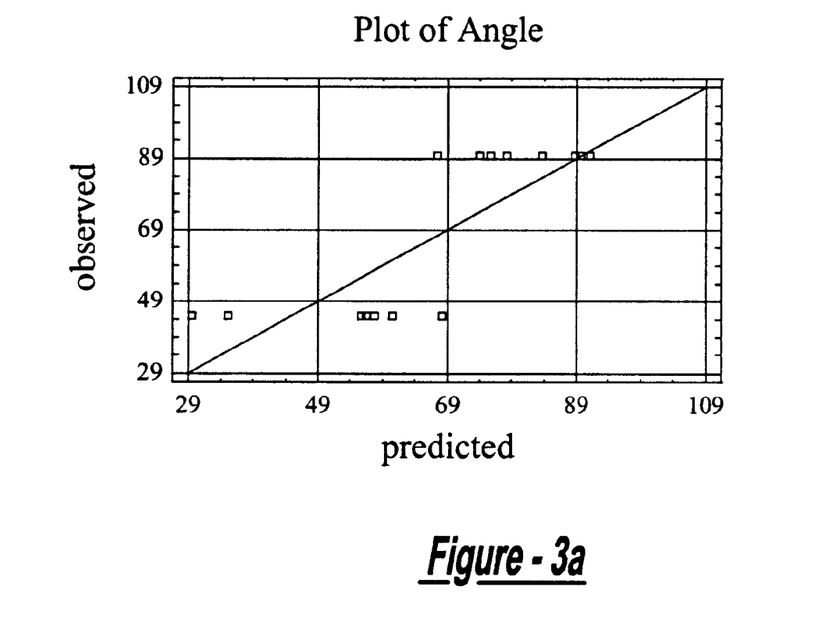
FIG. 3 illustrates x-y plots of predicted and observed values.
Figure 3B:
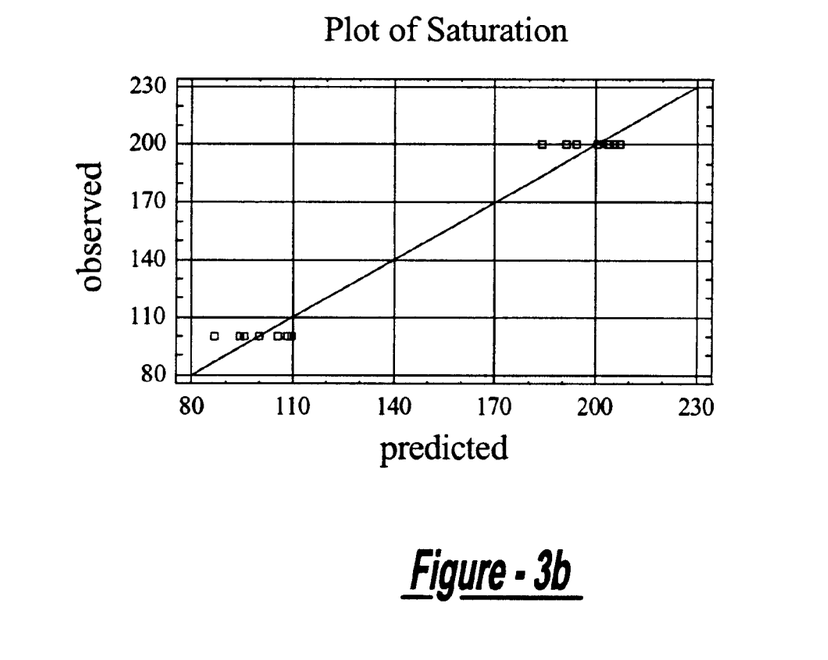
Figure 3C:
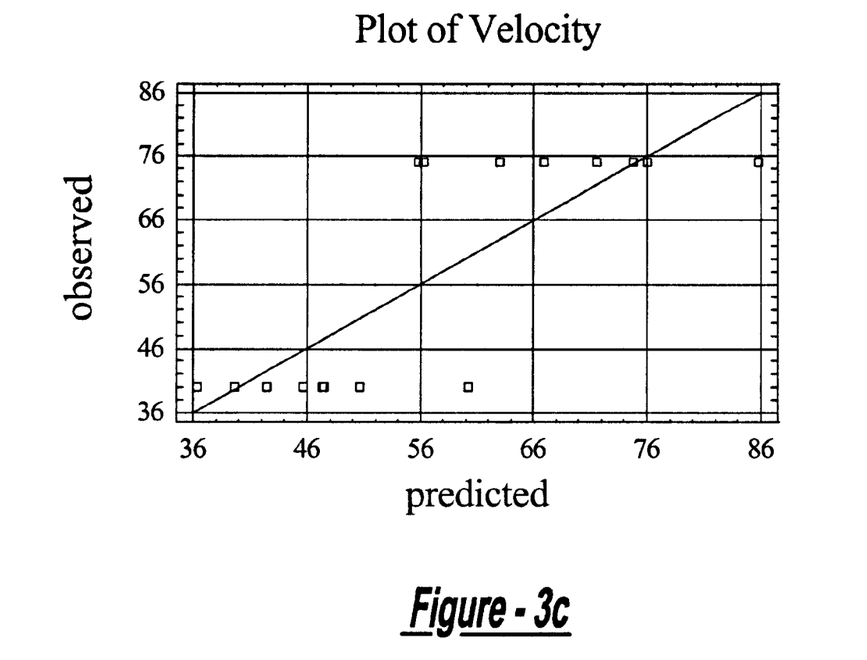
Figure 3D:
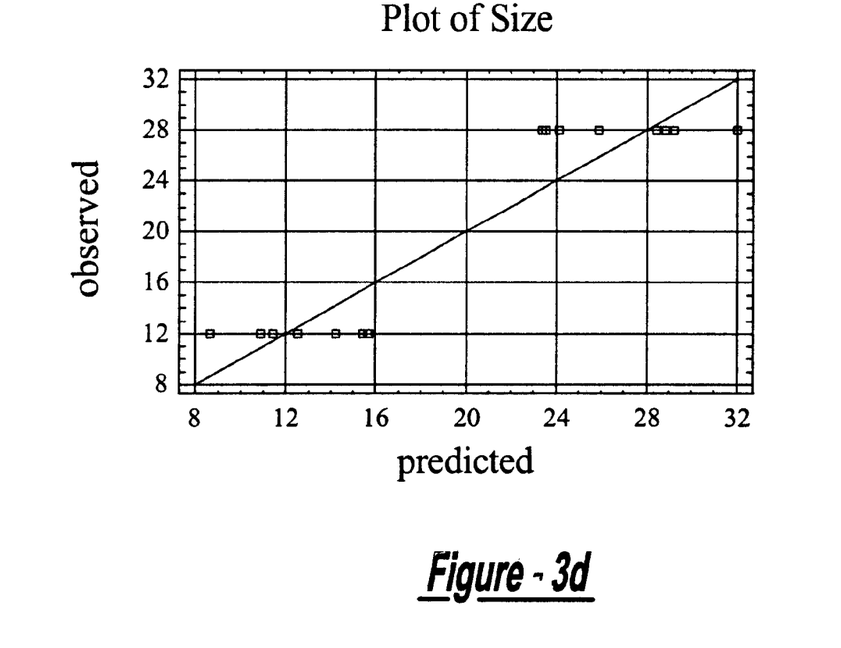

In the following example, the four parameters, Rsk, Rku, Rt and Stylus Y $\lambda$q were chosen. The four parameters represent difference aspects of the surface texture. For example, Rsk measures the symmetry of the surface material above or below the mean level. An Rsk of <0 implies a surface with more valleys than peaks. Rku, the kurtosis, differentiates the surface based on the sharpness of the peaks and valleys. A surface with either high narrow peaks/valleys will posses an Rku >3, whereas a surface composed of slowly varying, "rolling hills" will possess an Rku <3. The Rt parameter is simply the difference in height between the highest peak and lowest valley on the surface and thus represents the overall scale of the surface texture. Finally, Stylus Y $\lambda$q is a measure of the dominant spatial wavelengths that comprise the surface. A surface formed with large shot would tend to have a longer Stylus Y $\lambda$q than a surface formed by small shot. FIG. 2 is an example of how the four parameters may be used to depict the general nature of surface texture.

Once the four unique texture parameters are found, an advanced analytical technique known as principal component analysis is used to further create a set of parameters derived from the texture parameters that better model the process parameters directly.

The basic concept of principal components is to create a linear combination of the chosen texture parameters that are truly orthogonal (i.e. have very minimal correlation). Thus the technique (via STATGRAPHICS a mathematical software package) produces four new parameters:

Z1=F(Rsk, Rku, Rt, Stylus Y $\lambda$q)
Z2=G(Rsk, Rku, Rt, Stylus Y $\lambda$q)
Z3=H(Rsk, Rku, Rt, Stylus Y $\lambda$q)
Z4=I(Rsk, Rku, Rt, Stylus Y $\lambda$q)
Table 3-C. indicates the four parameters chosen for this work.

Note that the four texture parameters are first "standardized" as follows:

Standard Rsk=(Rsk−Average of all Rsk)/(Standard Deviation of all Rsk).
Standard Rku=(Rku−Average of all Rku)/(Standard Deviation of all Rku).
Standard Rt=(Rt−Average of all Rt)/(Standard Deviation of all Rt).
Standard Sty Y $\lambda$q=(Sty Y $\lambda$q−Ave of all Sty Y $\lambda$q)/(Std Deviation of all Sty Y $\lambda$q).

The standardization is a technique to center the data around the mean and to simplify the calculations. For example, after standardization, the average of all Rsk values to form the model will be Zero (0) and the standard deviation of all Rsk values used to form the model will be one (1). The standardized values are then read into STATGRAPHICS (note STATGRAPHICS is used in this illustration but other software packages may be used).

The four parameters (Z1, Z2, Z3, and Z4) are better suited to model the process parameters (e.g. shot size) than the individual components (e.g. Rsk). For example, for the data discussed above it is found that:

Z1=0.583*Rsk−0.600*Rku×0.022*Rt×0.547*Stylus Y $\lambda$q
Z2=−0.070*Rsk×0.314*Rku×0.865*Rt×0.385*Stylus Y $\lambda$q
Z3=−0.767*Rsk×0.252*Rku×0.216*Rt×0.550*Stylus Y $\lambda$q
Z4=0.258*Rsk×0.691*Rku×−0.453*Rt×0.500*Stylus Y $\lambda$q Once the four (or more or less) principal components are establish, a basic linear regression model is executed between the process variables and the various principal components. FIG. 3 demonstrates the various results for the example discussed above. Note that the $r^2$ values for the different analysis were 0.89, 0.52, 0.54 and 0.37 for Size, Angle, Saturation and Velocity respectively. Note that these $r^2$ values are not optimum and may be greatly improved by going to higher order models using terms such as $Z1*Z2$ and/or $Z1^2$ However, for the purposes of illustrating the technique a simple model using only first order terms (i.e. Z1, Z2, Z3, and Z4) is used here. The four equations that relate the principal components to the process parameters are then given by:

Size=20.0 +4.359*Z1+2.914*Z2+1.89*Z3+7.010*Z4
Angle=67.5+7.520*Z1+9.945*Z2+7.774*Z3+6.808*Z4
Saturation=150+9.574*Z1+2.694*Z2+53.36*Z3+1.714*Z4
Velocity=57.5+1.715*Z1+7.300*Z2+9.652*Z3+6.428*Z4

The graphs of FIG. 3 depict the "fit" of this simple linear model. As described above, these resulting equation are used here for illustration.

With the NDI model established, the model is executed to predict peening process parameters from measured surface texture parameters. For example, assuming the measured parameters are, Rsk=−0.44, Rku=3.84, Rt=4303 nm, and Stylus λq=83335nm.

The first step is to standardize the measured texture parameters to the mean and standard deviation of the data used to form the principal components model. For the values discussed here, the corresponding standardized texture parameters are:

$Rsk_s$=0.61, $Rku_s$=−0.60, $Rt_s$=−1.18, and $Stylu_s$, λq=−1.02

*Note that the subscript "s" implies a standardized value.

With the four standardized value established, they are inserted into the principal components equation to yield the new parameters:

Z1=0.583*0.61−0.600*(−0.60)+0.022*(−1.18)+0.547*(−1.02)
Z2=−0.070*0.61+0.314*(−0.60)+0.865*(−1.18)+0.385*(−1.02)
Z3=−0.767*0.61−0.252*(−0.60)+0.216*(−1.18)+0.550*(−1.02)
Z4=0.258*0.61+0.691*(−0.60)+−0.453*(−1.18)+0.500*(−1.02)

Resulting in:

Z1=0.132
Z2=−1.641
Z3=−0.622
Z4=−0.237

With the four components evaluated, they are then used in the multiple regression equations that were found earlier to directly predict the various process parameters:

Size=20.0+4.359*0.132+2.914*−1.641+1.89*−0.622+7.010*−0.237
Angle=67.5+7.520*0.132+−9.945*−1.641+7.774*−0.622−6.808*−0.237
Saturation=150+9.574*0.132+2.694*−1.641−53.36*−0.622−1.714*−0.237
Velocity=57.5−1.715*0.132+7.300*−1.641+9.652*−0.622+6.428*−0.237

Solving, the predicted values are found to be:

Size=13
Angle=82 deg
Saturation=180
Velocity=38
*Note that the actual values for the sample considered were:

Size=12
Angle=90 deg
Saturation=200%
Velocity=40 psi

Thus the example cited here demonstrates the predictive ability of the model versus the known peening conditions.

Once the complete NDI model was established, the 16 different peening conditions that were used to establish the model were tested for consistency with the model. Table 4, demonstrates the "Percent Error" in predicting the known process parameters with the measured texture parameters both for terms used to form the model and those not used.

TABLE 4

Results from the NDI example presented here for samples used to form the model and for samples not used to form the model

| RUN | Pred Vel % Error | Pred Ang % Error | Pred Sat % Error | Pred Size % Error |
|---|---|---|---|---|
| | Prediction Using Model Inputs - Self Check Principal Components (Rsk, Rku, Rt, Stylus Y λq) | | | |
| 1A | 63.5% | 33.3% | 7.2% | 22.9% |
| 2 | 8.6% | 5.1% | 32.1% | 6.9% |
| 3 | 17.7% | 21.3% | 49.5% | 10.8% |
| 4 | 22.2% | 18.7% | 0.5% | 6.5% |
| 5 | 31.4% | 20.5% | 17.3% | 2.3% |
| 6 | 18.7% | 4.8% | 13.4% | 23.1% |
| 7 | 5.6% | 9.3% | 9.9% | 8.0% |
| 8B | 40.2% | 6.1% | 21.8% | 22.3% |
| 9 | 30.6% | 89.3% | 45.8% | 18.7% |
| 10 | 6.7% | 29.4% | 25.9% | 8.8% |
| 11 | 45.9% | 8.0% | 38.6% | 9.2% |
| 12 | 0.1% | 15.8% | 0.2% | 7.0% |
| 13 | 25.3% | 51.5% | 0.9% | 14.8% |
| 14 | 4.7% | 21.3% | 7.0% | 0.0% |
| 15 | 11.9% | 13.8% | 14.7% | 3.5% |
| 16 | 16.7% | 3.4% | 36.7% | 16.4% |
| Ave Error | 21.9% | 22.0% | 20.1% | 11.3% |
| Max Error | 63.5% | 89.3% | 49.5% | 23.1% |
| Min Error | 0.1% | 3.4% | 0.2% | 0.0% |
| | Prediction Using samples not used to create the model Principal Components (Rsk, Rku, Rt, Sty Yq) | | | |
| C | 24.7% | 61.4% | 14.5% | 11.5% |
| D | 1.2% | 77.7% | 36.2% | 23.2% |
| E | 28.7% | 20.1% | 71.3% | 5.7% |
| F | 23.4% | 5.2% | 22.4% | 1.4% |
| G | 5.0% | 0.4% | 3.5% | 21.9% |
| Ave Error | 16.6% | 33.0% | 29.6% | 12.7% |
| Max Error | 28.7% | 77.7% | 71.3% | 23.2% |
| Min Error | 1.2% | 0.4% | 3.5% | 1.4% |

Table 4. Results from the NDI example presented here for samples used to form the model and for samples not used to form the model.

Once the shot-peening process variables are calculated then empirical data linking the process variables to fatigue life can be used to predict the fatigue life or other performance parameter of a impact treated or shot peened component. Thus there is a direct link between the surface morphology of the treated component and its performance characteristics.

It is to be understood that the invention is not limited to the exact construction illustrated and described above, but that various changes and modifications may be made without departing from the spirit and scope of the inventions as defined in the following claims.

We claim:

1. A nondestructive method for the inspection of impact treated surfaces to predict impact treatment process variables comprising:

acquiring a multi-dimensional map image of an impact treated surface;

characterizing said multi-dimensional map utilizing image processing to develop surface texture parameters; and developing relationships between said surface texture parameters and said impact treatment process variables.

2. The method of claim 1, wherein said step of developing relationships between said surface texture parameters and said impact treatment process variables comprises developing a relationship between surface texture parameters and shot peening process variables.

3. The method of claim 1 further comprising the step of evaluating said impact treatment process variables to determine performance parameters of said impact treated surface.

4. The method of claim 1 further comprising the step of evaluating said impact treatment process variables to determine residual compression of said impact treated surface.

5. The method of claim 1 further comprising the step of evaluating said impact treatment process variables to determine fatigue strength of said impact treated surface.

6. The method of claim 1 further comprising the step of evaluating said impact treatment process variable to determine stress corrosion resistance of said impact treated surface.

7. A nondestructive method for the inspection of impact treated surfaces to predict impact treatment process variables comprising:

acquiring a multi-dimensional map of an impact treated surface comprising taking an image with a camera system;

characterizing said multi-dimensional map to develop surface texture parameters; and developing relationships between said surface texture parameters and said impact treatment process variables.

8. The method of claim 7, wherein said camera system comprises a microscope system.

9. The method of claim 8, wherein said microscope system is an interferometric system.

10. A nondestructive method for the inspection of impact treated surfaces to predict impact treatment process variables comprising:

acquiring a multi-dimensional map of an impact treated surface;

characterizing said multi-dimensional map to develop surface texture parameters; and developing relationships between said surface texture parameters and said impact treatment process variables comprising:

applying correlation analysis to said surface texture parameters to determine which said surface texture parameters are statistically independent; and linking said statistically independent texture parameters with said impact treatment process variables.

11. The method of claim 10, wherein said step of applying correlation analysis comprise evaluating the degree of statistical independence via linear regression.

12. The method of claim 10, wherein said statistically independent surface texture parameters comprise;

Rsk, wherein said Rsk measures the symmetry of said impact treated surface above or below the mean surface level of said impact treated surface;

Rku, wherein said Rku represents the kurtosis which differentiates said impact treated surface based on the nature of peaks and valleys located on said impact treated surface;

Rt, wherein said Rt is the difference between the highest peak and lowest valley on said impact treated surface; and Stylus Y $\lambda$q, wherein Stylus Y $\lambda$q is a measure of the dominant spatial wavelengths that comprise said impact treated surface.

13. The method of claim 10 further comprising the step of standardizing said statistically independent texture parameters to establish equations that relate said statistically independent texture parameters to said impact treatment process variables.

14. An apparatus for inspecting a shot peened surface to predict process variables for a shot peening process comprising:

an imaging device which acquires multi-dimensional maps of said shot peened surface;

a signal processing device which characterizes said multi-dimensional maps to develop surface texture parameters which are used to predict said process variables for said shot-peening process.

15. The apparatus of claim 14, wherein said imaging device is a camera system.

16. The apparatus of claim 14, wherein said signal processing device includes a correlator which evaluates the degree of correlation between said surface texture parameters.

17. The apparatus of claim 14, wherein said surface texture parameters are generally statistically independent.

18. The apparatus of claim 14, wherein said signal processing device is a computer.

19. The apparatus of claim 14, wherein said process variables comprise shot size, saturation, shot velocity, and shot angle of impact.

20. An apparatus for determining the impact treatment process variables of an impact treated surface comprising:

an imaging system which captures the surface texture of said impact treated surface in a multi-dimensional image;

a processor which analyzes said multi-dimensional image to isolate a plurality of statistically independent variables, wherein said statistically independent variables describe said surface texture of said impact treated surface and are used to predict said impact treatment process variables.

21. The apparatus of claim 20, wherein said impact treated surface is shot peened.

22. The apparatus of claim 20, wherein said impact treated surface is laser treated.

23. The apparatus of claim 20, wherein said impact treated surface is ion treated.

24. The apparatus of claim 20, wherein said imaging system is a camera system.

25. The apparatus of claim 20, wherein said imaging system is a stylus.

* * * * *